US009427207B2

(12) United States Patent
Sheldon et al.

(10) Patent No.: US 9,427,207 B2
(45) Date of Patent: *Aug. 30, 2016

(54) MOTORIZED SYSTEMS AND METHODS FOR ACCESSING THE LUMEN OF A VESSEL

(71) Applicant: Houston Medical Robotics, Inc., Houston, TX (US)

(72) Inventors: Jeffery J. Sheldon, League City, TX (US); Kenneth R. Smith, League City, TX (US); Bruce W. Dannecker, League City, TX (US); Joseph M. Lacey, Hartselle, AL (US); Katherine E. Goodwin, Houston, TX (US)

(73) Assignee: HOUSTON MEDICAL ROBOTICS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,160

(22) Filed: Dec. 2, 2014

(65) Prior Publication Data

US 2015/0087992 A1    Mar. 26, 2015

Related U.S. Application Data

(62) Division of application No. 13/080,348, filed on Apr. 5, 2011, now Pat. No. 8,951,195.

(51) Int. Cl.
*A61B 17/34*    (2006.01)
*A61B 8/00*    (2006.01)
(Continued)

(52) U.S. Cl.
CPC ............... *A61B 8/0841* (2013.01); *A61B 5/14* (2013.01); *A61B 5/15003* (2013.01); *A61B 5/153* (2013.01); *A61B 5/150748* (2013.01); *A61B 8/14* (2013.01); *A61B 8/4209* (2013.01); *A61B 8/4444* (2013.01); *A61B 8/463* (2013.01);
(Continued)

(58) Field of Classification Search
CPC ............ A61B 17/3403; A61B 19/201; A61B 2017/3407; A61B 2017/3413; A61B 2019/5276; A61B 5/14; A61B 5/15003; A61B 5/140748; A61B 5/153; A61B 8/0841; A61B 8/0891; A61B 8/14; A61B 8/4209; A61B 8/4444; A61B 8/461; A61B 8/463; A61B 8/587; A61M 2005/1585; A61M 2005/1588; A61M 2025/0166; A61M 25/0105; A61M 25/0108; A61M 25/0111; A61M 25/0113; A61M 25/0606; A61M 25/065; A61M 25/09; A61M 25/09041; A61M 5/158; A61M 5/46
See application file for complete search history.

(56) References Cited

U.S. PATENT DOCUMENTS 8,945,011 B2 * 2/2015 Sheldon ............. A61B 17/3403
600/417
8,951,195 B2 * 2/2015 Sheldon ............. A61B 17/3403
600/417
(Continued)

*Primary Examiner* — Michael Rozanski
(74) *Attorney, Agent, or Firm* — Winstead PC

(57) ABSTRACT

An apparatus is utilized for accessing the lumen of a vessel. The apparatus includes a main body and a disposable cartridge. The main body includes a imaging device attachment, wherein the imaging device attachment is utilized to secure an image capturing instrument to the main body; a cartridge carrier coupled to the imaging device attachment, wherein the cartridge carrier is adjustable to achieve a target insertion depth; and a first motor coupled to the cartridge carrier, wherein the first motor adjust the cartridge carrier to achieve the target insertion depth. The disposable cartridge is attached to the cartridge carrier and houses a sheath, needle, or guidewire to be inserted into the vessel to the target insertion depth.

20 Claims, 12 Drawing Sheets

(51) Int. Cl.
*A61B 8/14* (2006.01)
*A61B 19/00* (2006.01)
*A61B 8/08* (2006.01)
*A61B 5/15* (2006.01)
*A61B 5/153* (2006.01)
*A61M 5/46* (2006.01)
*A61B 5/145* (2006.01)
*A61M 25/01* (2006.01)
*A61M 25/06* (2006.01)
*A61M 25/09* (2006.01)
*A61M 5/158* (2006.01)

(52) U.S. Cl.
CPC .......... *A61B8/587* (2013.01); *A61B 17/3403* (2013.01); *A61B 19/201* (2013.01); *A61M 5/46* (2013.01); *A61M 25/0108* (2013.01); *A61M 25/0606* (2013.01); *A61M 25/09* (2013.01); *A61B 8/0891* (2013.01); *A61B 8/461* (2013.01); *A61B 2017/3407* (2013.01); *A61B 2017/3413* (2013.01); *A61B 2019/5276* (2013.01); *A61M 5/158* (2013.01); *A61M 25/0111* (2013.01); *A61M 25/0113* (2013.01); *A61M 25/065* (2013.01); *A61M 25/09041* (2013.01); *A61M 2005/1585* (2013.01); *A61M 2005/1588* (2013.01); *A61M 2025/0166* (2013.01)

(56) References Cited

U.S. PATENT DOCUMENTS

| 9,033,880 | B2* | 5/2015 | Sheldon | A61B 8/462 600/437 |
| 2010/0010505 | A1* | 1/2010 | Herlihy | A61B 19/201 606/130 |
| 2013/0261553 | A1* | 10/2013 | Sheldon | A61B 8/0841 604/117 |
| 2015/0087970 | A1* | 3/2015 | Sheldon | A61B 17/3403 600/424 |

* cited by examiner

MOTORIZED SYSTEMS AND METHODS FOR ACCESSING THE LUMEN OF A VESSEL

RELATED APPLICATIONS

This application is a continuation of U.S. patent application Ser. No. 13/080,348, filed on Apr. 5, 2011, and issued as U.S. Pat. No. 8,951,195 on Feb. 10, 2015, which is incorporated herein by reference.

FIELD OF THE INVENTION

This invention relates to imaging assisted insertion of access of the lumen of vessels. More particularly, systems and methods discussed herein are related to the placement of a sheath, needle, and/or guidewire in a vessel.

BACKGROUND

Medical treatment may require the placement of catheters or the like into a person's body. For example, central venous catheters (also referred to herein as "CVC") are placed in a large vein for a variety of medical purposes. A series of manually performed steps that have remained largely unchanged to date. First, a hollow introducer needle is manually inserted through the skin and placed in the vein. Second, a guide wire is manually inserted through the hollow of the needle into the lumen of the vein. The guide wire is inserted until a portion of the guide wire extends past the end of the needle. In this position, the distal end of the wire is in the central vein and the proximal end is outside the patient's body. The introducer needle, which at this point has the guide wire running through its length, is then removed from the patient by pulling the needle out and over the wire. During removal of the needle, the distal end of the guide wire is undisturbed inside the lumen of vein. Third, the hollow CVC is placed over the proximal end of the guide wire, and the CVC advanced along the wire, through the skin, the subcutaneous tissues, and into the vein. At its final position, the catheter will have one end in the vein and the other end outside of the body. The guide wire can now be retrieved by pulling the guide wire through the catheter and out of the body, without disturbing the position of the catheter. The catheter can now be used to access to the central venous circulation. This process relies on the medical practitioner to locate the vein and may require several attempts before the CVC is properly placed. Similarly, other medical procedures may require placement of a sheath, needle, and/or guidewire into the lumen of a vessel. Medical practitioners may encounter similar problems when attempting to place a sheath, needle, and/or guidewire into the lumen of a vessel.

More recently, ultrasound has been used to assist in the placement of a CVC in a vein. Ultrasound can used to locate the venous lumen and provide a visual target. The CVC may be placed manually or a robotic device may be used to place the CVC. Even with ultrasound guidance, a medical practitioner may fail to properly place the CVC. Further, current robotic devices are significantly large, cumbersome, and costly and their use in the placement of CVC is impractical.

SUMMARY

In one implementation, an apparatus for accessing the lumen of a vessel is provided. The apparatus includes a main body and a disposable cartridge. The main body includes a imaging device attachment, wherein the imaging device attachment is utilized to secure an image capturing instrument to the main body; a cartridge carrier coupled to the imaging device attachment, wherein the cartridge carrier is adjustable to achieve a target insertion depth; and a first motor coupled to the cartridge carrier, wherein the first motor adjust the cartridge carrier to achieve the target insertion depth. The disposable cartridge is attached to the cartridge carrier and houses a sheath, needle, or guidewire to be inserted into the vessel to the target insertion depth.

In another implementation, a method for accessing the lumen of a vessel is provided. The method includes the steps of attaching an image capturing instrument to an imaging device attachment of a main body, and attaching a disposable cartridge to the main body. The main body includes a imaging device attachment, wherein the imaging device attachment is utilized to secure an image capturing instrument to the main body; a cartridge carrier coupled to the imaging device attachment, wherein the cartridge carrier is adjustable to achieve a target insertion depth; and a depth motor coupled to the cartridge carrier, wherein the depth motor adjust the cartridge carrier to achieve the target insertion depth. The method also includes determining a depth of the vessel with an imaging device, wherein the depth of the vessel is the target insertion depth; adjusting the main body to achieve the target insertion depth; and actuating a controller, wherein the controller causes a sheath, needle, or guidewire in the disposable cartridge to advance a first predetermined distance.

In yet another implementation, an apparatus for accessing the lumen of a vessel is provided. The apparatus includes a main body and a disposable cartridge. The main body includes a body providing an image device attachment and a cartridge carrier pivotally attached to the body, wherein the cartridge carrier provides at least one motor. The main body also includes a controller coupled to the motor, wherein actuating the controller inserts a sheath, needle, or guidewire to a target depth. The disposable cartridge includes a sheath slidably coupled to the disposable cartridge, wherein the sheath is advanced and retracted by the motor, and a needle slidably coupled to the disposable cartridge, wherein the needle is advanced and retracted by the motor, and the needle extends to a target insertion depth when fully advanced. The disposable cartridge also includes a guidewire coupled to the disposable cartridge, wherein the guidewire is advanced by the motor.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1A:
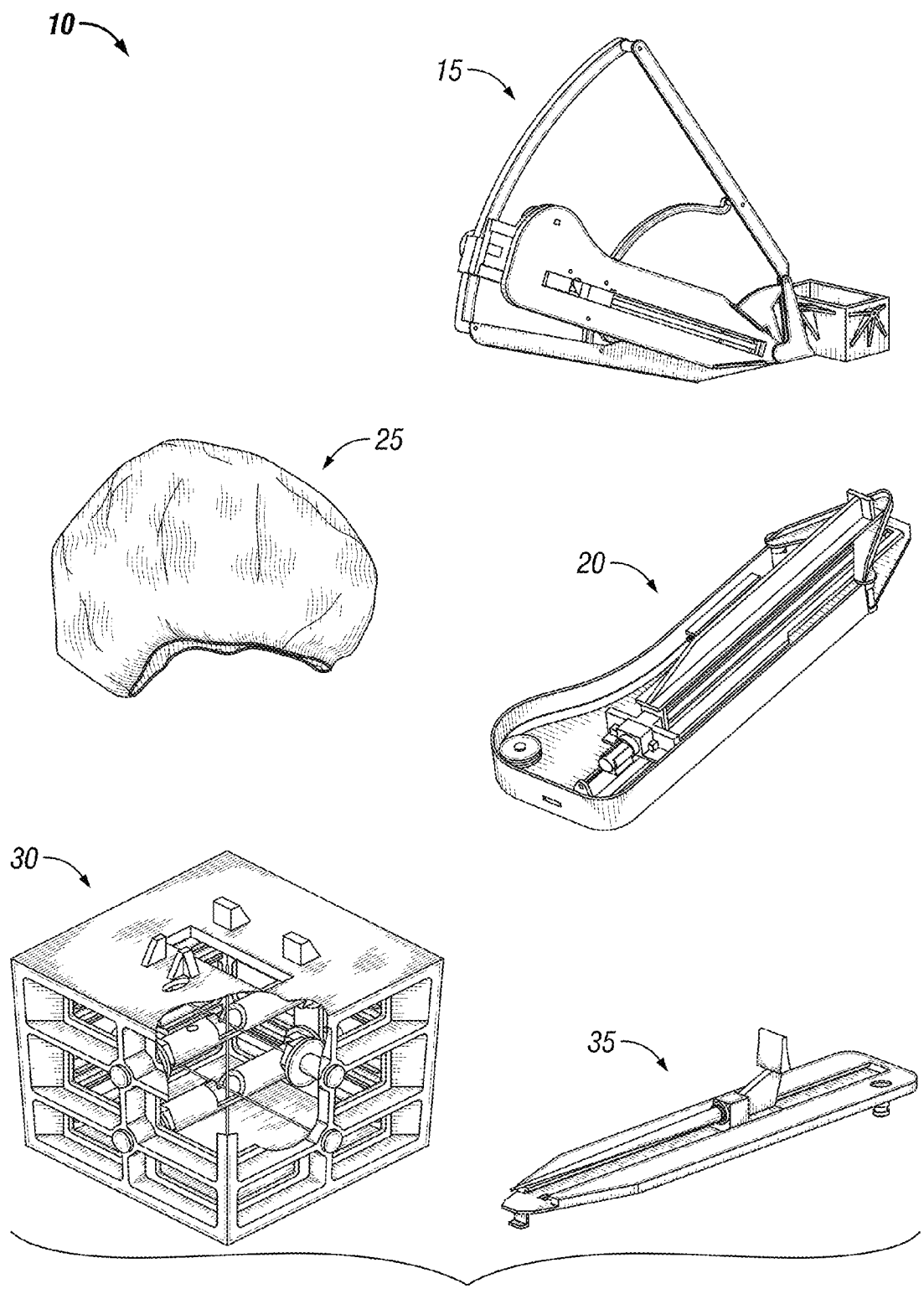
FIGS. 1A and 1B are an illustrative implementation of a motorized insertion system.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The systems and methods discussed herein are designed to integrate with a commercially available imaging system (e.g. ultrasound system) to provide a medical practitioner with the capability to accurately and reliably accessing the lumen of a vessel located at a depth of 5 mm to 60 mm below the skin surface. For example, the systems and methods discussed herein may be utilized to place a central venous catheter (CVC). While the implementations discussed herein may discuss usage of the systems and methods for starting a CVC, it will be recognized by one of ordinary skill in the art that the scope of the invention is in no way limited to starting a CVC. For example, in other implementations, the system may be utilized to place needle in a vessel; to place a guidewire via a needle placed in a vessel; or to place a sheath via a guidewire that is placed in a vessel via a needle. The systems and methods discussed herein may be utilized in a variety of medical procedures, including, but not limited to: CVC placement, peripherally inserted central catheters, phlebotomy, dialysis access, cardiac catheterization, amniocentesis, cholecystotomy, thoracentesis, paracentesis, and tracheostomy. The insertion system is portable, reusable, robotic, and easily operated.

Figure 1B:
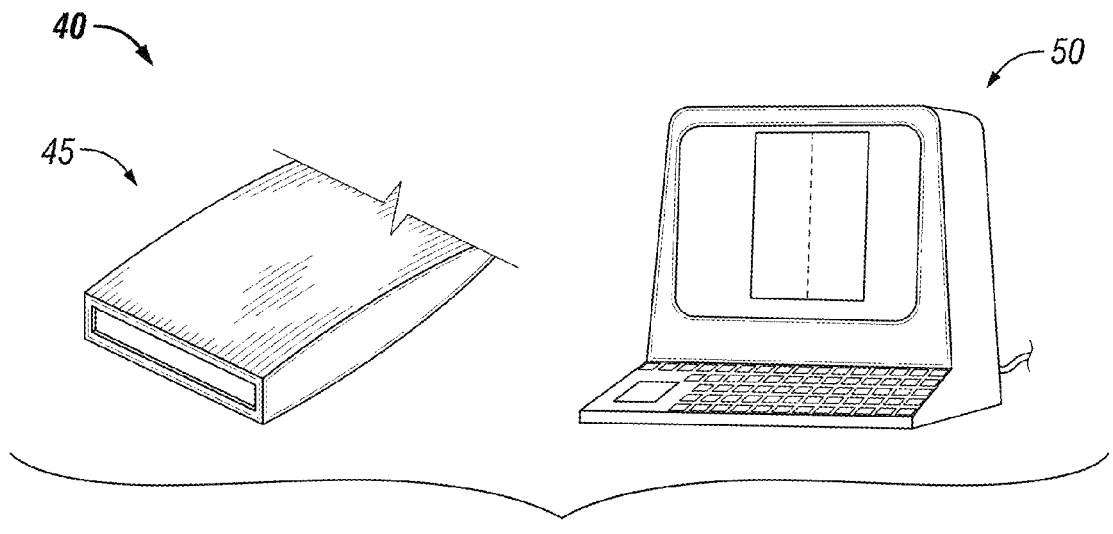

FIGS. 1A and 1B are an illustrative implementation of a motorized insertion system 10. Motorized insertion system 10 may include a main body 15, disposable cartridge 20, cover 25, alignment cube 30, and alignment cartridge 35. Motorized insertion system 10 is suitable for use with an imaging device 40 that may include an image capturing instrument 45 and image display 50. For example, imaging device 40 may be an ultrasound imaging device with a transducer utilized to capture images and a display presenting the captured images. Imaging device 40 is independent and separate from motorized insertion system 10. Because motorized insertion system 10 is separate from the imaging device, any suitable imaging device may be utilized with motorized insertion system. This may allow a pre-existing imaging device that a medical practitioner may already own to be utilized with motorized insertion system 10.

Main body 15 provides a platform that receives several components that are utilized during the sheath insertion process. For example, disposable cartridge 20, alignment cube 30, alignment cartridge 35, and/or image capturing instrument 45 may be attached or coupled to main body 15 during various steps in the sheath, needle, and/or guidewire insertion process. Main body 15 utilized several motors to move, adjust, and control components of motorized insertion system 10 during the insertion process as discussed herein.

Disposable cartridge 20 can be coupled to main body 15 and may include a needle, guidewire, catheter, and other components utilized to place a CVC or the like. Cover 25 is sterile and may be place on main body 15 to prevent contamination or the like. Cover 25 may be placed on or around main body 15 and disposed of after usage. Alignment cube 30 is utilized to properly align image capturing instrument 45 when it is coupled to main body 15. Alignment cartridge 35 can be coupled to main body 15 and is utilized to perform a check on the alignment of main body 15.

Figure 2A:
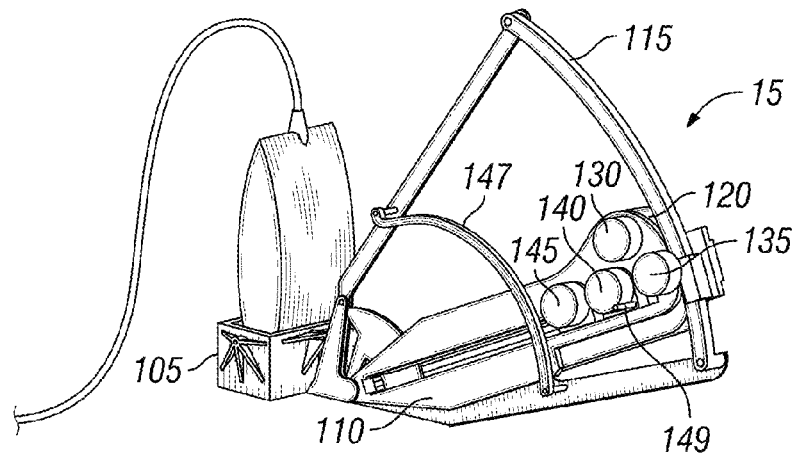
FIGS. 2A and 2B are illustrative implementations of a main body.
Figure 2B:
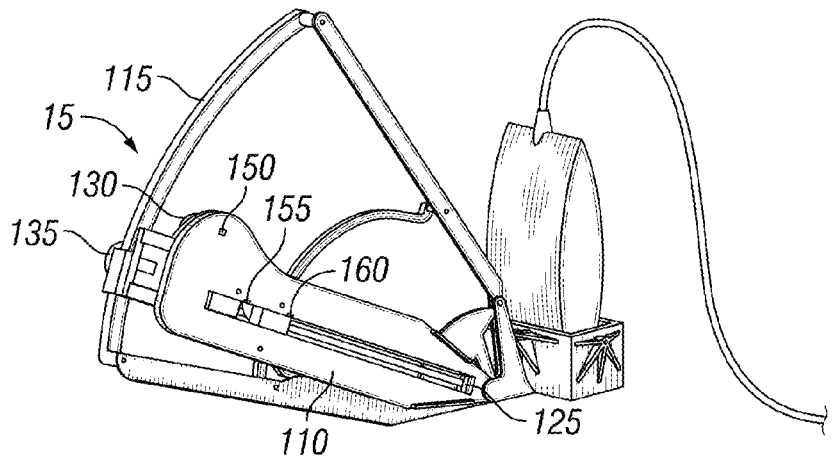

FIGS. 2A and 2B are illustrative implementations of a main body 15. For the purposes of illustration and clarity, main body 15 is shown without an imaging device and cover. An imaging device, such as an ultrasound, can be coupled to main body 15, but it should be noted that the imaging device is not part of main body 15. This arrangement allows any suitable brand or type of imaging device to be utilized with handheld device 15. For example, an ultrasound transducer may be secured to main body 15 in preparation for use of the insertion system, and removed when desired.

Main body 15 may include an imaging device attachment 105, cartridge carrier 110, arc arm 115, cartridge 120, attachment points 125, guidewire motor 130, angle motor 135, needle motor 140, sheath motor 145, guidewire actuator 150, needle actuator 155, and sheath actuator 160. Imaging device attachment 105 is utilized to secure image capturing instrument 45 of imaging device 40 to main body 15. For example, an ultrasound transducer may be placed in imaging device attachment 105 and secured to main body 15. Main body 15 may provide attachment points 125 to hold and support cartridge 120 on cartridge carrier 110. For example, cartridge 120 may be an alignment cartridge or disposable cartridge. A first end of cartridge carrier 110 is pivotally attached to main body 15 near image device attachment 105. The opposite end of cartridge carrier 110 is coupled to arc arm 115. A stop bar 147 is provided by main body 15. Stop bar 147 is an arc-like bar positioned on main body 15 between imaging device attachment 105 and arc arm 115. An extension 149 extends from needle actuator 155. As shown, stop bar 147 is positioned along the pathway of needle actuator 155 so that extension 149 will contact stop bar 147 when the needle actuator 155 is advanced forward. Angle motor 135 on cartridge carrier 110 may be coupled to arc arm 115 as well to adjust the angle of cartridge carrier 110. For example, angle motor 135 may be coupled to a gear or wheel that rotates to adjust the angle of arc arm 115. Further, arc arm 115 may include gear teeth that mate with the teeth on the gear or wheel coupled to angle motor 135. Arc arm 115 may provide depth scale indicating the depth of insertion for a particular angle of cartridge carrier 110.

Guidewire motor 130 is coupled to guidewire actuator 150 on cartridge carrier 110. When a cartridge 130 with a guidewire is properly attached to cartridge carrier 110, guidewire motor 130 may actuate guidewire actuator 150 to advance or retract the guidewire. Needle motor 140 is coupled to needle actuator 155 on cartridge carrier 110. When a cartridge 130 with a needle is properly attached to cartridge carrier 110, needle motor 140 may actuate needle actuator 155 to advance or retract the needle. Sheath motor 145 is coupled to sheath actuator 160 on cartridge carrier 110. When a cartridge 130 with a sheath is properly attached to cartridge carrier 110, sheath motor 145 may actuate needle actuator 160 to advance or retract the sheath. Guidewire motor 130, angle motor 135, needle motor 140, and sheath motor 145 may be coupled to a power source. For example, main body 15 may attach to a power cable that may be plugged into a power outlet or main body 15 may include a rechargeable battery pack.

In order to control the operation of guidewire motor 130, angle motor 135, needle motor 140, and sheath motor 145, main body 15 may provide a plurality of controllers. The controllers may be buttons, switches, joysticks, thumbsticks, a keypad, a combination thereof, or any other suitable controls. For example, each individual motor may be controlled by a separate controller or by a combined controller that allows an operator to advance and/or retract a guidewire, needle, or sheath. Further, a motor may be utilized to adjust the angle of cartridge carrier 110. Guidewire motor 130 may have a corresponding guidewire controller. Angle motor 135 may have a corresponding angle/depth controller. Needle motor 140 may have a corresponding needle controller. Sheath motor 145 may have a corresponding sheath controller. Guidewire, needle, and sheath controllers may allow an operator to advance or retract the component, whereas angle/depth controller may allow the operator to adjust the angle of cartridge carrier 110 to adjust for a targeted insertion depth. In some implementations, an operator may operate the controller to adjust the angle of cartridge carrier 110 to a desired target depth shown on a depth scale. In other implementations, an operator simply enters a desired target depth into the controller, which causes main body to automatically adjust to the targeted depth. In another implementation, a single motor is utilized to provide the functionality of guidewire motor 130, angle motor 135, needle motor 140, and sheath motor 145. The single motor may be connected to a gear case that is capable of switching between modes that allow the motor to control the guidewire, needle, sheath, and the angle of cartridge carrier 110.

Figure 3A:
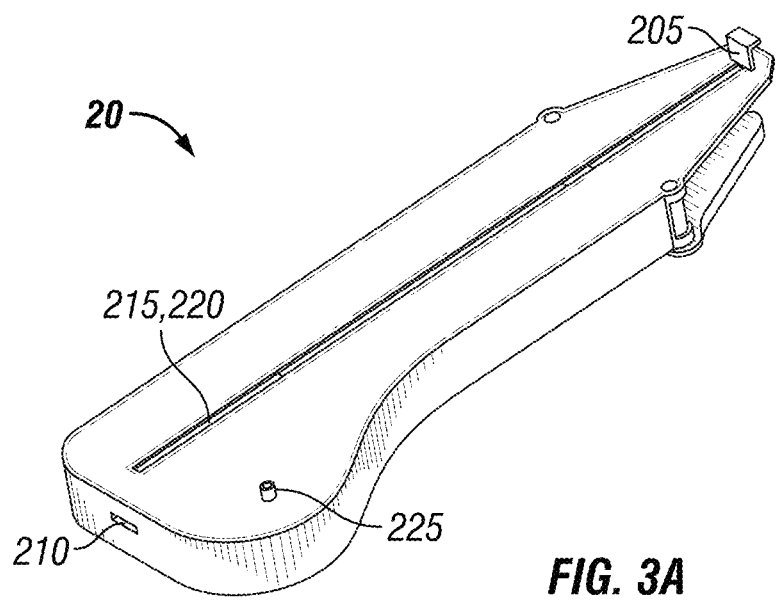
FIGS. 3A and 3B are illustrative implementations of a disposable cartridge.
Figure 3B:
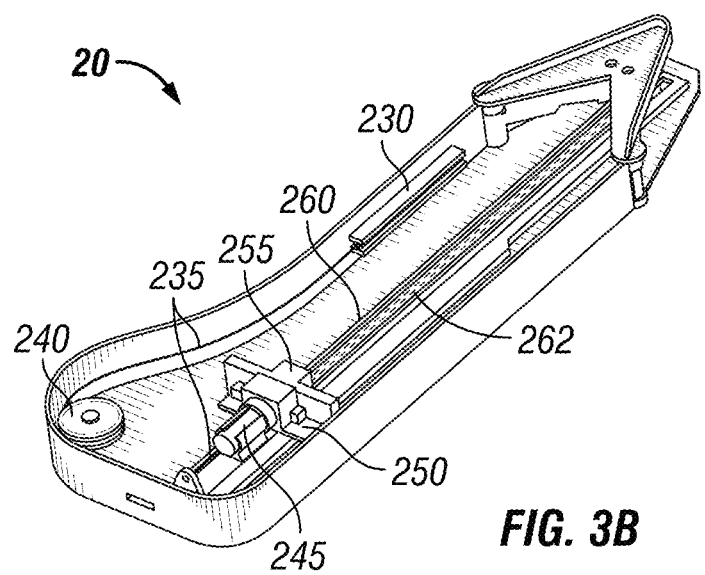

FIGS. 3A and 3B are illustrative implementations of a disposable cartridge 20. Disposable cartridge 20 is sterile to prevent the spread of bacteria, disease, etc. Disposable cartridge 20 is disposed after a single use. However, in other implementations, a cartridge may be subject to a cleaning and disinfection process after each use. Disposable cartridge 20 may include an attachment bracket 205, attachment slot 210, needle interface 215, sheath interface 220, guidewire interface 225, guidewire track 230, guidewire 235, guidewire wheel 240, needle hub 245, sliding truck 250, sheath hub 255, and sheath 260. Attachment bracket 205 and attachment slot 210 are utilized to secured disposable cartridge 20 to cartridge carrier 110. Needle interface 215 and sheath interface 220 of disposable cartridge 20 mate with needle actuator 155 and sheath actuator 160 of cartridge carrier 110. This allows needle actuator 155 in cartridge carrier 110 to move a needle in disposable cartridge 20 and sheath actuator 160 in cartridge carrier 110 to move sheath 260 in disposable cartridge 20. Guidewire interface 225 mates with guidewire actuator 150, thereby allowing guidewire motor 130 to advance and retract guidewire 235.

Guidewire 235 passes through guidewire track 230 to guidewire wheel 240, which advances or retracts guidewire 235. Guidewire 235 passes through the center of needle hub 245 down through the center of sheath 260 and the needle 262. Needle 262 is positioned in the center of sheath 260 and may slide into and out of sheath 260. In some implementations, a dilator may be provide in between needle 262 and sheath 260 to minimize or prevent bending of needle 262. Needle hub 245 is attached to needle interface 215, sliding truck 250, and the needle. When needle interface 215 is advanced or retracted by needle motor 140, it causes the needle, needle interface 215, and sliding truck 250 to advance or retract as well. Sheath hub 255 is connected to sheath 260 and sheath interface 220. When sheath motor 140 advances or retracts sheath interface 220, it causes the sheath hub 255 and sheath 260 to advance or retract as well. Note, sliding truck 250 and sheath hub 255 are not connected. Because sliding truck 250 and sheath hub 255 travel along the same path, advancing sliding truck 250 into sheath hub 255 also causes the sheath hub to advance. However, retracting sliding truck 250 does not cause sheath hub 255 to retract.

Figure 4:
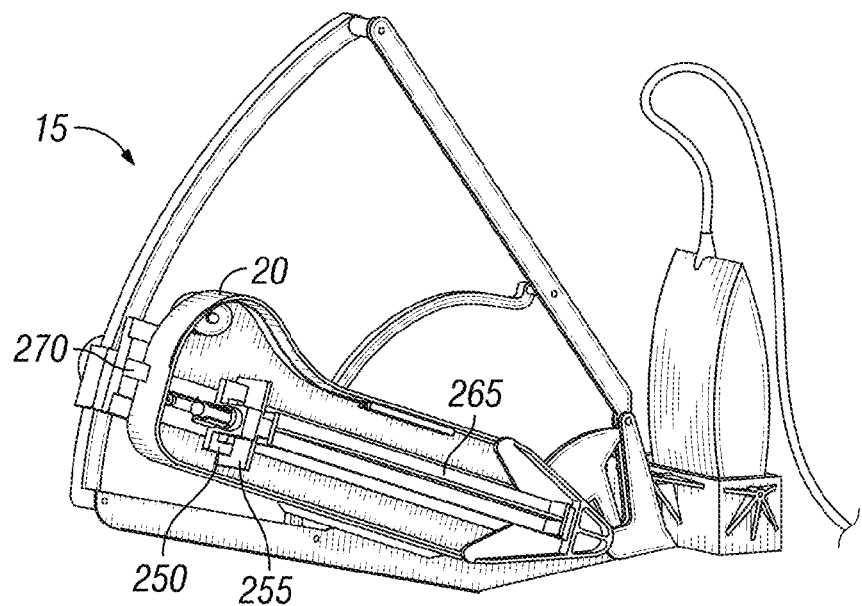
FIG. 4 is an illustrative implementation of a main body with a disposable cartridge attached.

FIG. 4 is an illustrative implementation of a disposable cartridge 20 placed in main body 15. Lock bar 265 is designed to secure sheath 260, needle, and/or associated medical components in a desired position to prevent undesired movement before the lock bar is removed. Lock bar 265 prevents sliding truck 250 and sheath hub 255 from advancing in disposable cartridge 20. For example, during shipping, before attachment to the reusable handheld device, and/or prior to use it is desirable to prevent a sharp needle and sheath from protruding from disposable cartridge 20. However, when disposable cartridge 20 is attached to main body 20 that is ready for use, lock bar 265 may be removed to allow sliding truck 250, sheath hub 255, and associated medical components to be freely advanced and retracted. Attachment clip 270 secures disposable cartridge 20 to main body 15. Attachment clip 270 fits into attachment slot 210 on disposable cartridge 20 when properly attached.

Figure 5:
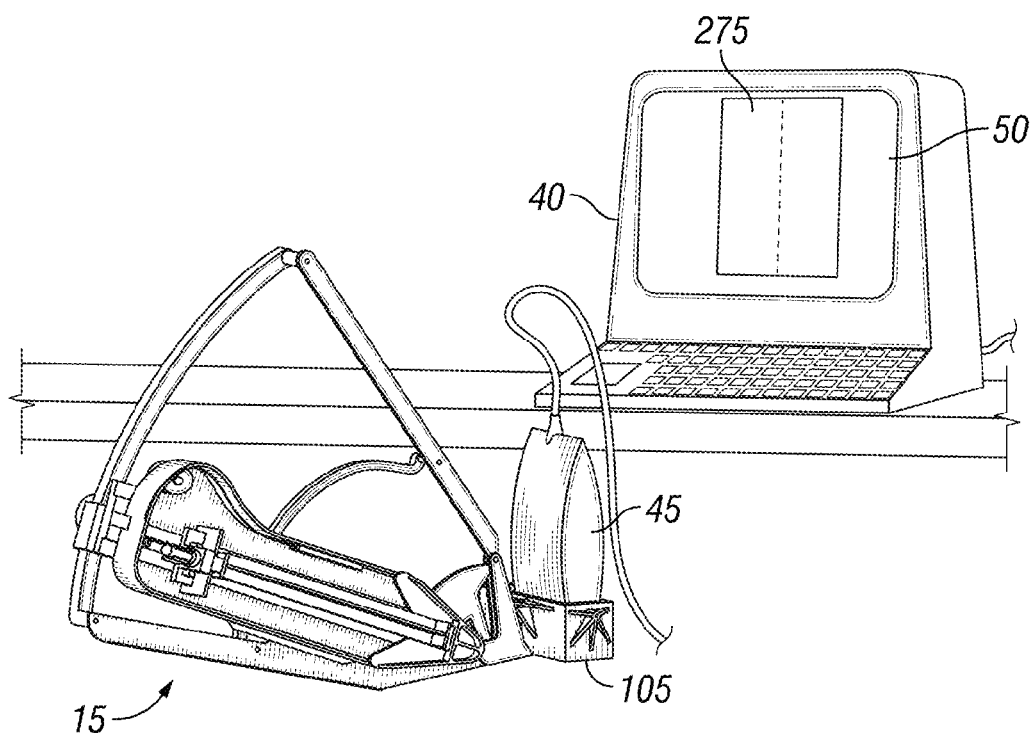
FIG. 5 is an illustrative implementation of a main body and imaging device.

FIG. 5 is an illustrative implementation of a main body 15 and imaging device 40. Imaging device 40 may include an image capturing instrument 45 that may be secured in imaging device attachment 105 of main body 15. Image capturing instrument 45 may send and/or received signals utilized to generate images. Imaging device 40 receives data from image capturing instrument 45 and shows the generated images on display 50. For example, a commercially available ultrasound imaging device may be utilized and the ultrasound transducer may be secured in imaging device attachment 105 of the main body 15. Screen overlay 275 is a transparent adhesive film that may include a vertical dashed line in the center and may provide tick marks (not shown) on each side. Screen overlay 275 is designed to fit on and adhere to a display 50 of imaging device 40. Screen overlay 275 provides an operational reference for use of motorized insertion system 10.

Screen overlay 275 may be a clear, thin, plastic sheet with low tack adhesive that can be affixed to a display 182 of imaging device 40. Screen overlay 275 may provide a vertical dashed center line. In some implementations, screen overlay 275 may also provide tick marks on each side that provides a visual reference aid to the user. Screen overlay 275 and imaging device 40 allow the medical practitioner to accurately locate a vessel and determine the depth of the vessel. The medical practitioner may then set motorized insertion system 10 to the measured depth by actuating a depth controller that controls angle motor 135. It should be noted that an image capturing instrument 45 of the imaging device 40 connects to main body 15, but imaging device 40 is not part of the motorized insertion system 10. Since medical facilities may already have a suitable imaging device, utilizing an existing imaging device, rather than incorporating the imaging device, reduces cost. This also allows the sheath insertion methods and systems discussed herein to easily be adapted for use with a variety of different types and/or brands of imaging devices. Imaging devices that are suitable for use with the insertion systems discussed herein will preferably be capable of imaging and measuring depths of approximately 5 mm to 60 mm.

Figure 6:
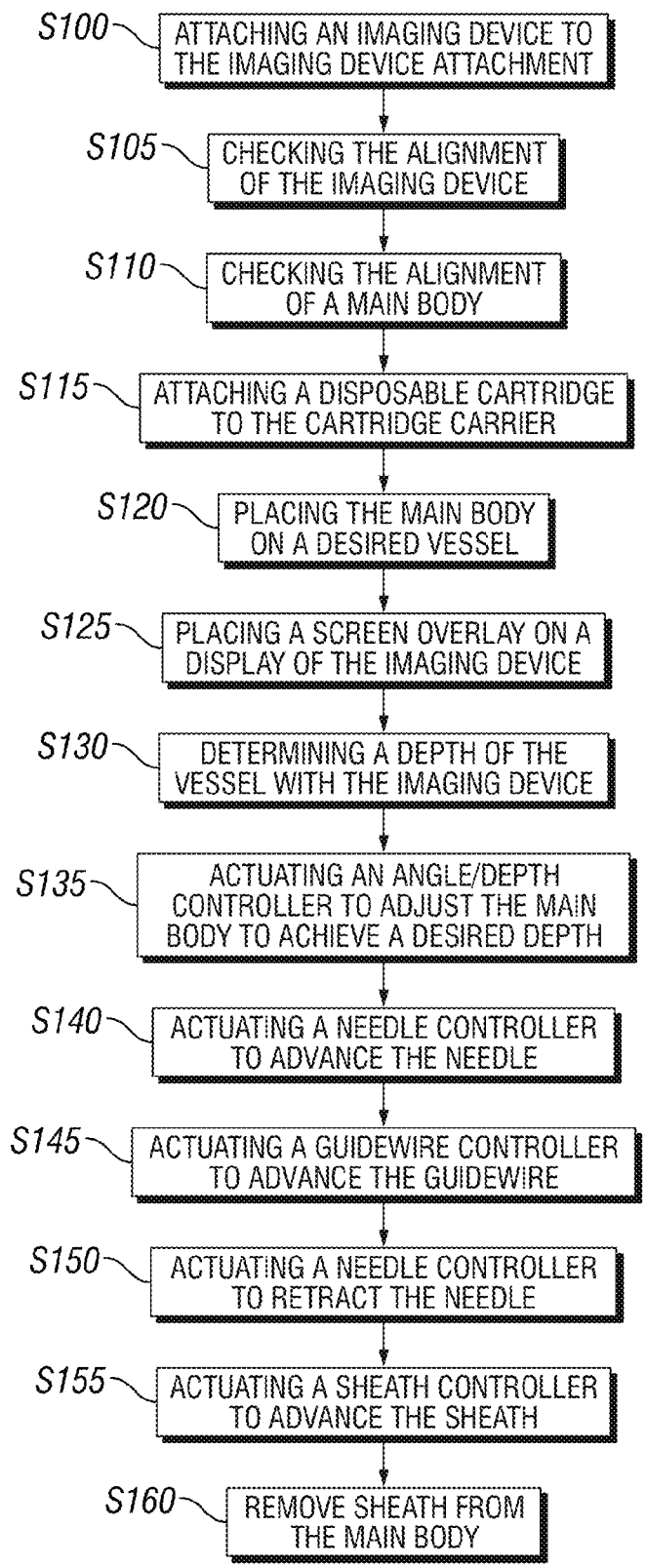
FIG. 6 is an illustrative implementation of a method for inserting a sheath into a vessel with a motorized sheath insertion device.

FIG. 6 is an illustrative implementation of a method for inserting a sheath into a vessel with a motorized insertion system. Many of the steps for the method discussed herein may be performed in a different sequence than shown or may be omitted. The scope of methods for inserting a sheath into a vessel is in no way limited to the particular methods illustrated herein. One of ordinary skill in the art will recognize a variety of potential variations in the sequence and particular steps performed. While the following provides a description of inserting a sheath into a vessel, it will be recognized by one of ordinary skill in the art that the device is suitable for a variety of medical procedures involving the insertion of a sheath, needle, and/or guidewire into the lumen of a vessel. The scope of the claims is in no way limited to inserting a sheath into a vessel, except where expressly stated in the claims. For example, in other implementations, the insertion system may simply be utilized to place a needle in the lumen of a vessel or to place a guidewire in the lumen of a vessel with the aid of a needle.

To prepare motorized insertion system 10 for use, the operator may integrate the main body 15 with imaging device 40 in step S100 by placing image capturing instrument 45 in imaging device attachment 60 and securing it with the thumb screws or the like. In step S105 the alignment of the main body 15 may be checked using an alignment cartridge. In step S110 the alignment of the imaging device can be check using an alignment cube. In other implementations of a sheath insertion method, screen overlay 275 may be placed on the display of the imaging device during these alignment checks rather than in step S125. Aligning the reusable handheld device and imaging device with an alignment cartridge and cube are discussed in further detail below. Note that the alignment steps S105 and S110 are optional steps that are performed for best results. However, in the case that alignment checks have been previously performed in the same day or recently, it may not be necessary to perform the alignment checks.

Disposable cartridge 100 can be attached to cartridge carrier 110 of main body 15 in step S115. Next, main body 15 can be placed on a desired vessel location to find a target vessel in step S120. The display of the imaging device will provide an image of a desired location. In step S125, the operator may adjust reusable handheld device so the target vessel is centered on the vertical dotted line of screen overlay 275. The operator may then utilize the imaging device to determine the target depth of the vessel in step S130. The target depth indicates the distance from the top surface (or skin of the patient) to the center of the vessel. When the target depth of the vessel is determined, the operator can actuate an angle/depth controller to modify the insertion depth of the needle to a desired depth in step S135. The angle/depth controller may be an actuator or the like that controls the angle of cartridge carrier 110. Depending on the particular type of actuator being utilized, the operator may actuate the angle/depth controller until the desired depth is reached on a depth scale provided on arc arm 115 or may simply input the desired depth to allow main body 15 to automatically adjust to achieve the desired depth. Once the operator has set the device to achieve the desired depth, the operator may actuate a needle controller to advance the needle into the patient in step S140. Note that advancing the needle also causes sheath 260 to advance, but does not cause sheath 260 to enter the patient.

Once the needle is fully advanced, the operator may actuate a guidewire controller to advance the guidewire 235 through the needle into the target vessel in step S145. Now that guidewire 235 is in the target vessel, the needle actuator can be actuated to retract the needle in step S150. Next, the operator may actuate a sheath controller to advanced sheath 260 along guidewire 235 into the patient and target vessel in step S155. Finally, in step S160, sheath 260 can be removed from main body 15, thereby completing placement of the sheath in the target vessel.

Two alignment tasks may be performed to check the alignment of the insertion system. The first step in the alignment process is performed as part of the preparation procedure to ensure correct positioning of the image capturing instrument in the imaging device attachment. The second step in the alignment check is performed to ensure the mechanical structure and sliders on the reusable handheld device are in correct positions. Both alignment tasks can be performed in a non-sterile or sterile environment.

Figure 7:
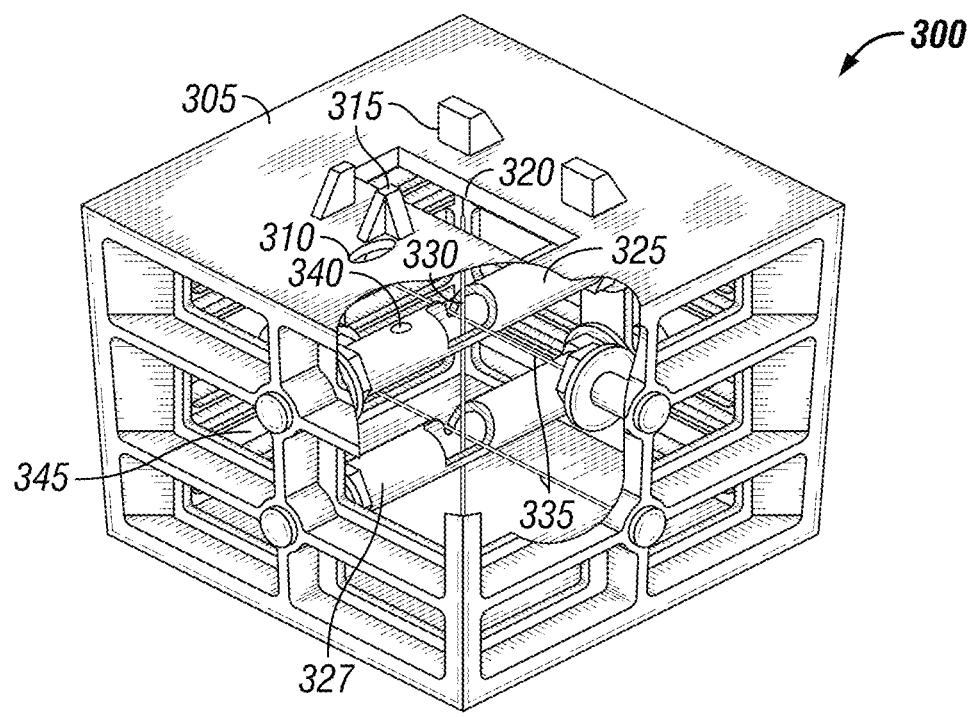
FIG. 7 is an illustrative implementation of an alignment cube.

FIG. 7 is an illustrative implementation of an alignment cube 300. Alignment cube 300 enables the user to perform alignment tasks. Top lid 305 of alignment cube 300 provides a needle insertion port 310, alignment guides 315, and image capturing window 320. Needle insertion port 310 provides an entry point for the needle/stylet to enter alignment cube 300. Alignment guides 315 receive the imaging device attachment 105 of the reusable handheld device and serve to properly align the reusable handheld device to alignment cube 300. Image capturing window 320 provides an opening for the image capturing instrument 45 of the imaging device. Image capturing window 320 is directly above the target points of shallow vessel target (X-Axis) 325 and deep vessel target (X-Axis) 327 in alignment cube 300.

The shallow vessel target 325 is positioned at a depth of 30 mm and the deep vessel target 327 is positioned at a depth of 60 mm. The shallow vessel target 325 and deep vessel target 327 are arranged perpendicular to the image capturing window 320 and horizontal to the top lid 305, defining the x-axis of the alignment cube 300. Both the shallow vessel target 325 and deep vessel target 327 in the alignment cube 300 includes a premeasured and marked target center point. In particular, the target center points are indicated by wire structures intersecting shallow vessel target 325 and deep vessel target 327. Target wire (Y Axis) 330 is arranged vertically or along the y-axis in alignment cube 300. Two target wires (Z-Axis) 335 are arranged perpendicular to the shallow vessel target 325 and deep vessel target 327 along the z-axis in alignment cube 300. Target wire (Z-Axis) 335 are perpendicular to shallow vessel target 325, deep vessel target 327 and target wire (Y-Axis) 330. The shallow vessel target 325 at a depth of 30 mm may include a stylet window 340 that allows the stylet to pass through to the deep target vessel 327. This stylet window 340 allows the needle/stylet to reach deep vessel target 327 at a depth of 60 mm. Alignment cube 300 may include several viewing windows 345, or the sides of the cube may be made of a transparent material, to allow a user to view the alignment process of the main body 15. Alignment cube 300 and the shallow vessel target 325 and deep vessel target 327 can be filled with water by the user to accommodate the imaging signal.

Figure 8:
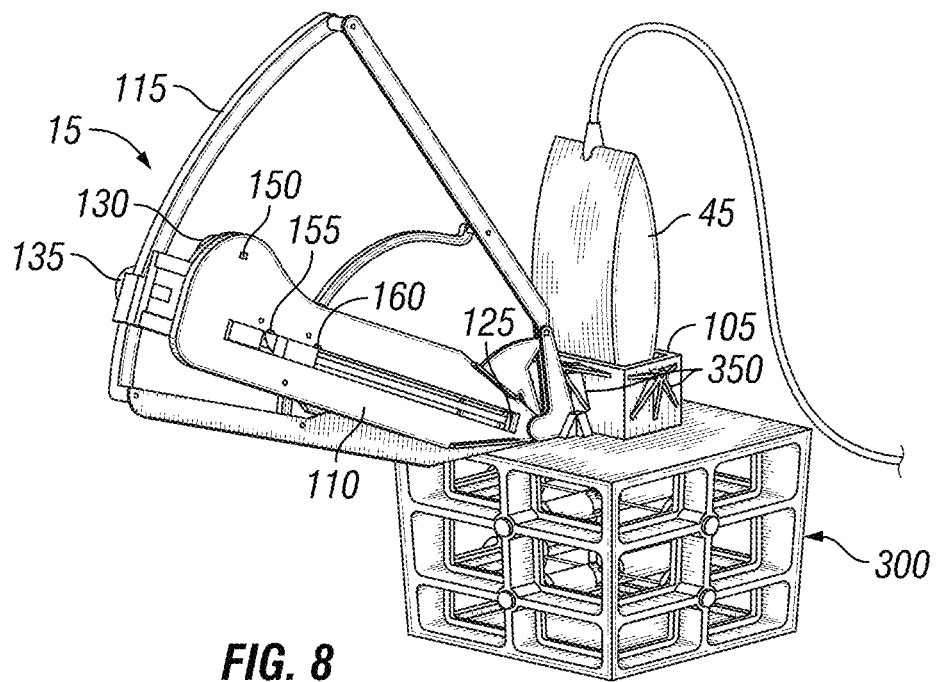
FIG. 8 is an illustrative implementation of a reusable handheld device placed on top of an alignment cube.

FIG. 8 is an illustrative implementation of a main body 15 placed on top of an alignment cube 300. The first step in the alignment process is to attach the image capturing instrument 45 to the main body 15 and secure it in place with the thumbscrews 350. Note that image capturing instrument 45 and main body 15 should be cleaned and disinfected prior to the first alignment check. With the image capturing instrument 45 attached, the user can power on the imaging device. After filling the alignment cube with water, the main body may be placed on top of the alignment cube. Image capturing instrument 45 is repositioned in the imaging device attachment 105 to make sure that it is positioned correctly and properly aligned.

In order to properly align image capturing instrument 45, target vessels 325, 327 and target wires 330, 335 should be properly aligned on the display of the imaging device. Once target vessels 325, 327 and target wires 330, 335 are properly aligned on the display, screen overlay 275 should be positioned in alignment with target vessels 325, 327 and target wires 330, 335 displayed on imaging device 40. For example, screen overlay 275 may be position on display 50 as shown in FIG. 5. When image capturing instrument 45 and screen overlay 275 are properly aligned, the vertical dashed centerline of screen overlay 275 corresponds to a plane of the needle and sheath.

Figure 9:
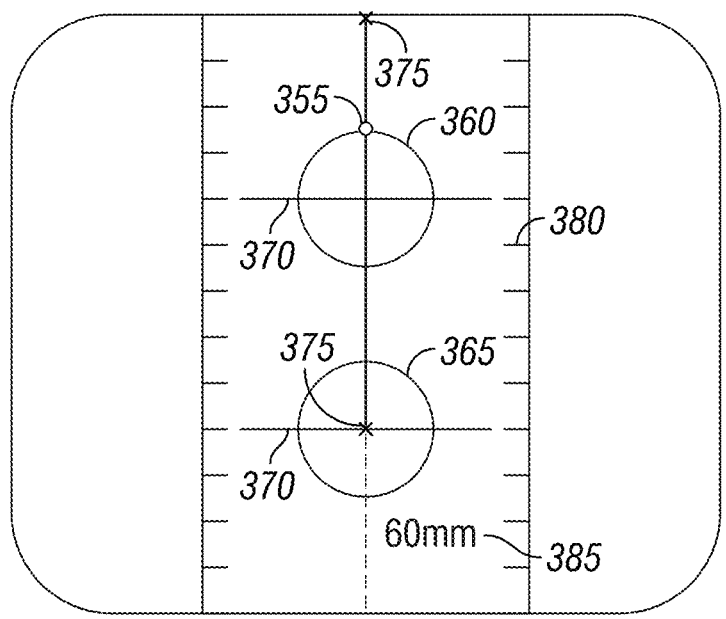
FIG. 9 is an illustrative implementation of a image displayed on an imaging device when a reusable handheld device is placed on top of an alignment cube.

FIG. 9 is an illustrative implementation of a image displayed on an imaging device when a main body 15 is placed on top of an alignment cube 300. When image capturing instrument 45 is properly aligned, the image resulting from placing main body 15 on top of an alignment cube 300 should resemble FIG. 9. The ultrasound system display should show two circles 360, 365 aligned vertically in the center of the screen representing the shallow and deep target vessels 325, 327 at 30 mm and 60 mm in alignment cube 300, respectively. Each of the circles 360, 365 will have a bright horizontal line 370 through the center. Vessel targets 325, 327 have target wires 335 travelling along the z-axis of alignment cube 300 passing through them. Target wires 335 are represented by horizontal lines 370 passing though the top circle 360 and bottom circle 365. During the alignment check, the user can rotate the image capturing instrument 45 about the x-axis until horizontal lines 370 in the 30 mm and 60 mm vessel simulation are horizontal. Horizontal tick marks 380 may be provided by screen overlay 375 to help the operator determine a horizontal position. The user may then pitch the image capturing instrument 45 about the z-axis until the circles 360, 365 are clear and a small white circle 355 representing target wire 330 appears at the top center of the 30 mm vessel simulation image circle 360.

Holding that position, the user or an assistant can hand tighten thumb screws 350 on the imaging device attachment 105. Screen overlay 275 should be placed on the screen so that the center line dissects circles 360,365 through small white circle 355 at the top center and horizontal lines 370 looks horizontal when compared to the side tick marks. The final check of the alignment process is to use the depth measuring capability of the ultrasound system to measure the depth of the Z-axis vessel simulation wire at 60 mm. This is done by placing a mark 375 on the top of the display and another mark 375 (vertically aligned) on the image of the Z-axis of the 60 mm vessel simulation. Measured distance 385 computed by the imaging device 40 should match the known depth of the wire i.e. 60 mm. Similarly, a check may be performed on the vessel target at 30 mm.

Figure 10:
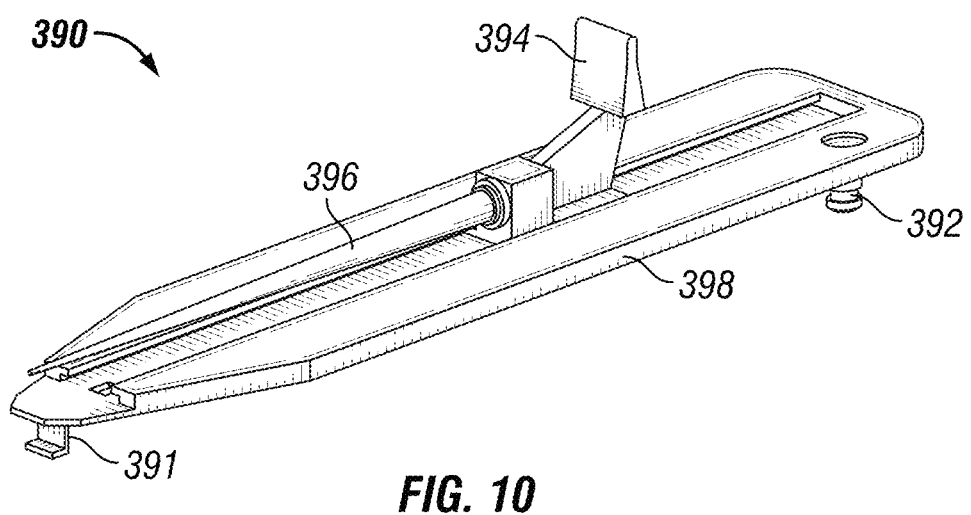
FIG. 10 is an illustrative implementation of an alignment cartridge.

The purpose of the second alignment check procedure is to ensure that the mechanical structure and sliders have not moved out of position due to misuse or damage. FIG. 10 is an illustrative implementation of an alignment cartridge 390. Alignment cartridge 390 can be used to perform the alignment check procedure. Alignment cartridge 390 has the same interfaces and attachment points as the disposable cartridge, but does not contain any medical components. Similar to the disposable cartridge, attachment tab 391 and locking pin 392 are utilized to attach alignment cartridge 390 to the reusable handheld device. Alignment cartridge 390 provides a stylet slider 394 attached to a stylet 396 that is the same length as the needle in the sterile disposable cartridge. Cartridge base 398 provides an opening that receives stylet slider 394 and allows stylet slider 394 to be advanced and retracted.

The user begins the procedure in a non-sterile or sterile environment by placing the image capturing instrument 45 in imaging device attachment 105 and securing it in place with the thumb screws 350. With image capturing instrument 45 securely in place, the user attaches the alignment cartridge 390 to the main body 15. After filling the alignment cube 300 with water, the user can follow the previously discussed alignment steps discussed above, if necessary, to align the position of the image capturing instrument if necessary. However, note that a screen overlay is not required to perform the alignment check procedure.

When the image capturing alignment or first alignment check is successfully completed, the user can set the main body 15 to a depth of 30 mm and actuate stylet slider 394 on alignment cartridge 390. When the stylet slider 394 stops advancing, the distal end of stylet 396 should touch the intersection point at 30 mm between z-axis wire 335 and y-axis wire 330. Visual confirmation of this is made by looking through the viewing windows on the sides of the alignment cube. The user can then repeat this procedure for the intersection point at 60 mm between the z-axis wire 335 and y-axis wire 330. If visual confirmation indicates that the stylet does not touch the intersection points of the wires at 30 mm or 60 mm, the reusable handheld device is recalibrated and adjusted for proper alignment.

An example of a method for inserting a sheath into a vessel is discussed in detail below. In particular, the method discussed utilizes an ultrasound imaging device with motorized insertion system 10. Initially, first and second alignment checks are performed with alignment cube 300 and alignment cartridge 390 as described previously. With the alignment checks complete, the insertion system is ready for use on the patient. Preparation may include, if necessary, positioning the patient, disinfecting the procedure site, draping the procedure site, administering anesthesia, and the like. The final patient preparation step is the application of sterile ultrasound gel to the procedure site. With patient preparation complete, the user applies the sterile ultrasound gel to the image capturing instrument 45 and attaches the sterile disposable cartridge 20 to main body 15. With gel correctly applied to the image capturing instrument 45 and sterile disposable cartridge 20 attached, the user positions sterile cover 25 over main body 15 and image capturing instrument 45. With the cover correctly positioned, the user can place main body 15 on the patient at the procedure site and begin to receive ultrasound images of the patient's vessel(s) displayed on the display. The ultrasound imaging display, with screen overlay 275, allows the user to adjust main body 15 until the desired target vessel is centered on the vertical dotted line on screen overlay 275 or the target plane of needle and sheath 260. The user can use the distance measuring capability of the ultrasound imaging device to measure the depth to the center of the target vessel. Additionally, the user can use the distance measuring capability of the ultrasound imaging device to measure the semi-major axis and semi-minor axis of the vessel image to determine the diameter of the target vessel. The depth of the vessel should be between 5 mm and 60 mm, and the diameter of the vessel should be at least 4 mm in diameter. If the depth or diameter is inappropriate, the user should select a different place along the vessel where the depth and diameter are satisfactory. To set main body 15 to the depth value obtained from the depth measurement, the user actuates a depth controller that causes angle motor 135 to adjust cartridge carrier 110 the targeted depth. With depth setting on the main body 15 achieved, the user may then actuate a needle controller that causes needle motor 140 to advance needle interface 215 in disposable cartridge 20. This inserts needle into the patient and places the needle in the center of the target vessel. With needle fully advanced into the patient's vessel, the user can actuate a guidewire controller that causes guidewire motor 130 to actuate guidewire interface 225, thereby causing guidewire 235 to advance through needle into the patient. The user can evaluate the placement of the guidewire via the ultrasound image display 50.

With guidewire 235 fully advanced into the patient's vessel, the user can actuate the needle controller to fully retract the needle away from the patient. This will retract the needle completely back into disposable cartridge 20 and out of sheath 260. The user can then actuate a sheath controller that causes sheath motor 145 to advance sheath interface 220, thereby advancing sheath 260 along guidewire 235 into the target vessel.

With sheath insertion complete, the user can remove sheath 260 from disposable cartridge 20. While holding sheath 260 and guidewire 235 in place, the user may remove main body 15 from the patient. As main body 15 is moved away from the patient, the proximal end of guidewire 235 slides through the needle and separates from disposable cartridge 20. Disposable cartridge 20 is then removed from main body 15 and disposed. Image capturing instrument 45 and main body 15 may then be separated from each other, cleaned, disinfected, and stored.

Figure 11A:
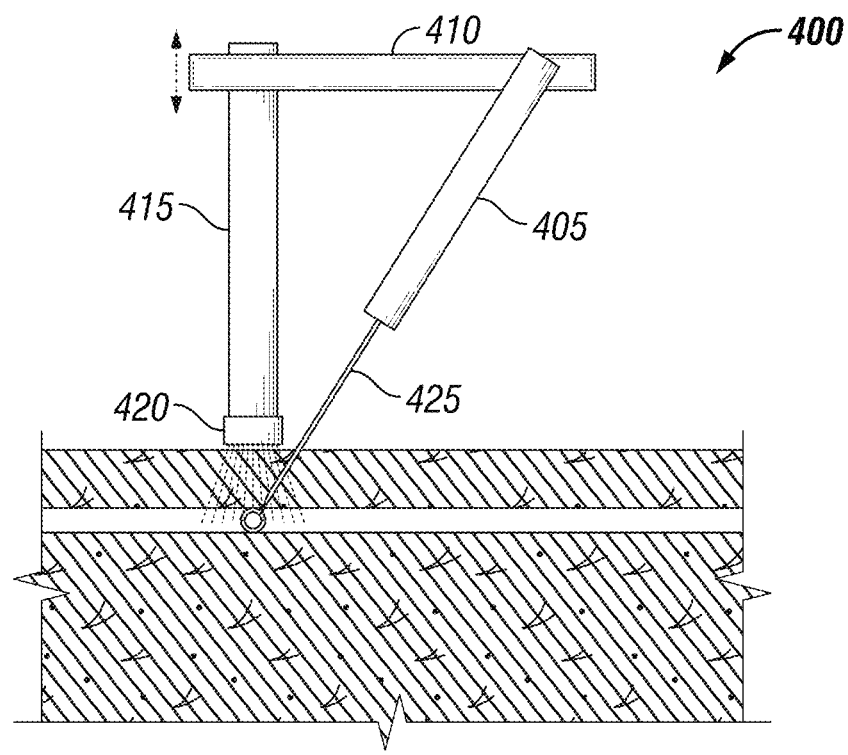
FIGS. 11A and 11B are illustrative implementations of a second arrangement for an insertion system.
Figure 11B:
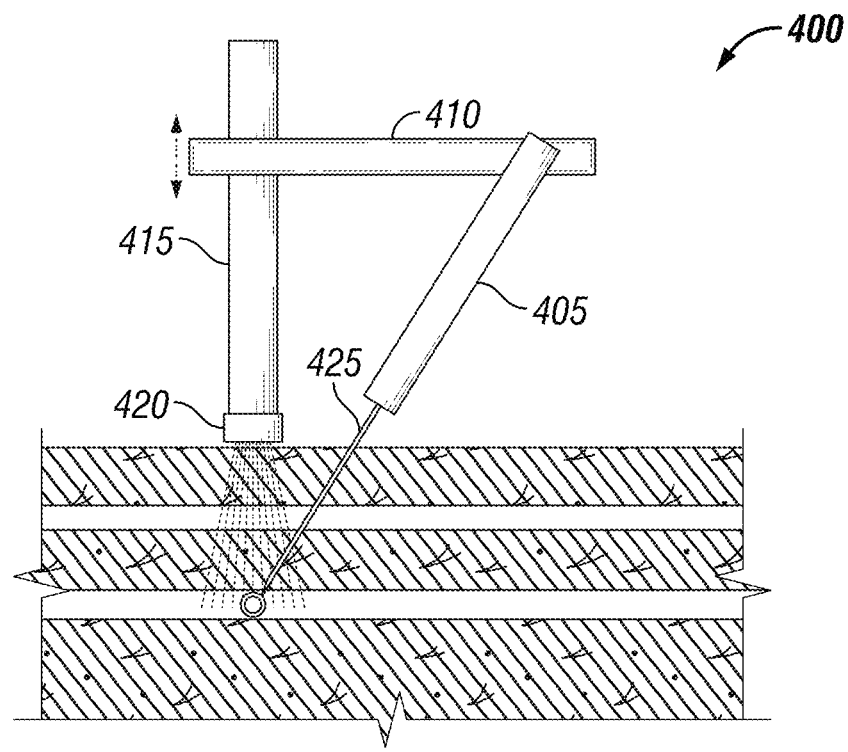

FIGS. 11A and 11B are illustrative implementations of a second arrangement for an insertion system 400. In insertion system 400, cartridge 405 is fixed at a predetermine angle. While cartridge 405 is shown independently attached to boom 410, in other implementations, cartridge 405 may be secured to fixed arm in a similar manner as to the articulating arm 45 shown in FIG. 4. Cartridge 405 may be coupled to adjustable boom 410, which may be adjusted vertically to achieve different target depths. Boom 410 is coupled to transducer arm 415. Transducer arm 415 may provide a depth scale that indicates the needle depths of the range of heights for boom 410. Transducer arm 415 provides an attachment for transducer 420. Needle 425 extends to a fixed predetermined length.

Figure 12A:
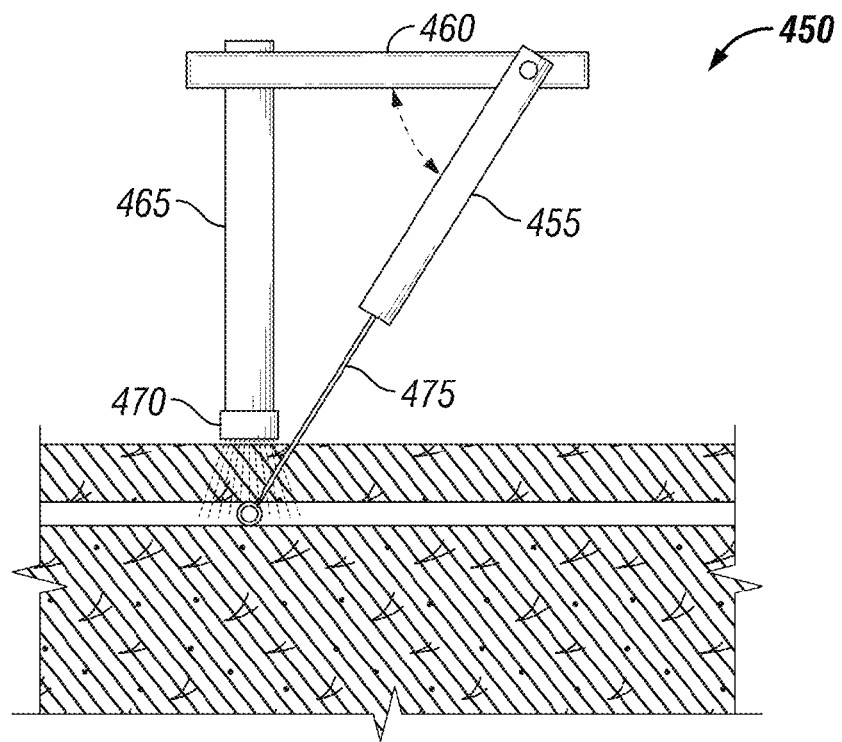
FIGS. 12A and 12B are illustrative implementations of a third arrangement for an insertion system.
Figure 12B:
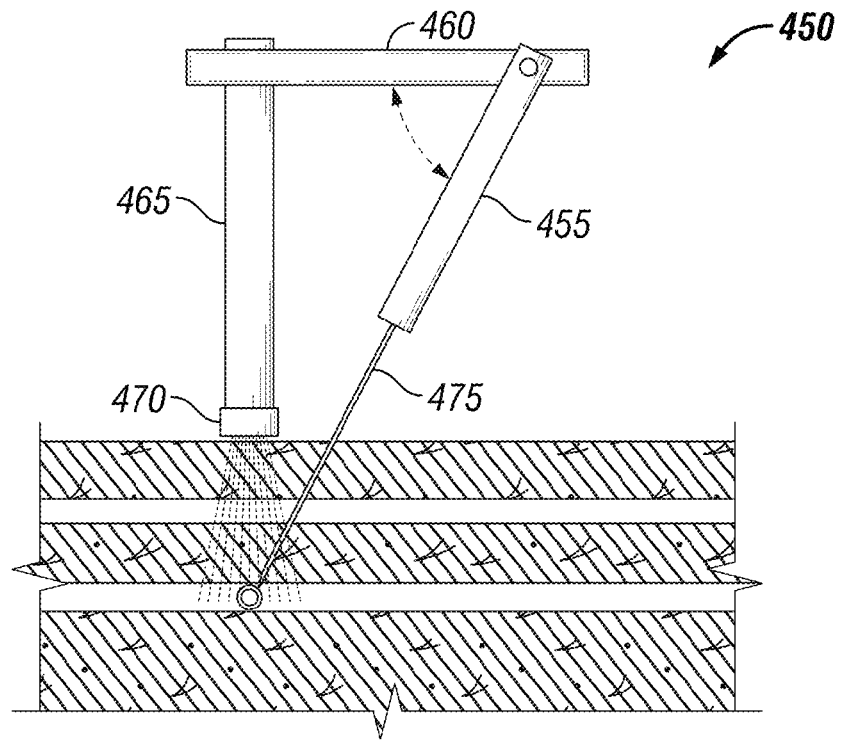

FIGS. 12A and 12B are illustrative implementations of a third arrangement for an insertion system 450. In insertion system 450, cartridge 455 has a variable angle in relation to boom 460. While cartridge 455 is shown independently attached to boom 460, in other implementations, cartridge 455 may be secured to fixed arm in a similar manner as to the articulating arm 45 shown in FIG. 4. In contrast to the previous implementation, boom 460 is a fixed height. Boom 460 is coupled to transducer arm 465, which provides an attachment for transducer 470. Needle 475 is a variable length needle. As the angle of cartridge 455 increase, the depth of insertion increases. The angle of cartridge 455 and length of needle 475 are adjusted to achieve a desired target depth. A depth scale (not shown) for insertion system 450 takes into account the angle of cartridge 455. The depth scale may indicate the depth of needle 475 based on the angle of cartridge 455 and the amount needle 475 has been extended.

Figure 13A:
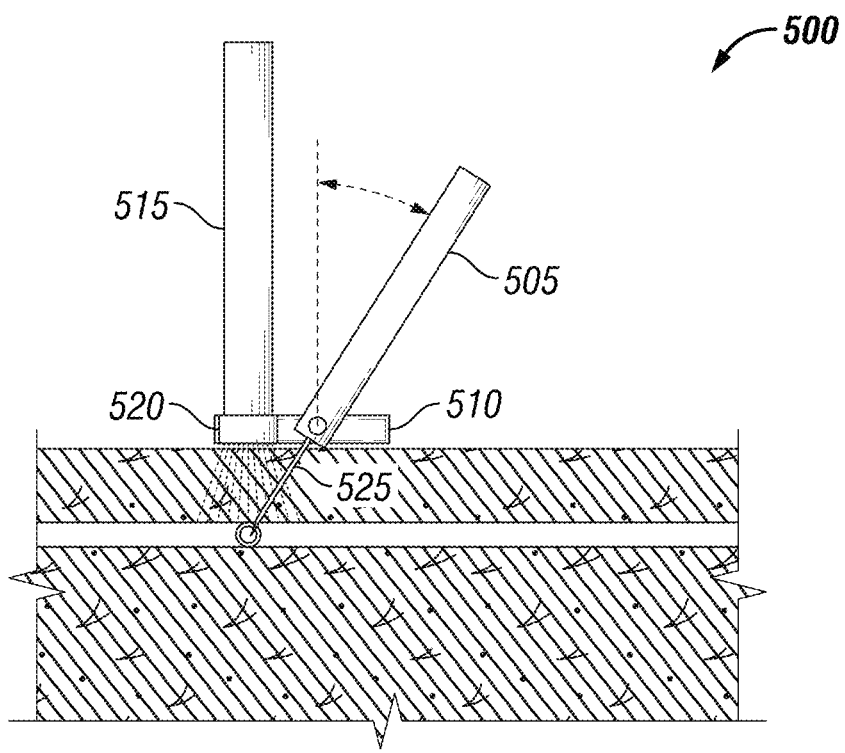
FIGS. 13A and 13B are illustrative implementations of a fourth arrangement for an insertion system.
Figure 13B:
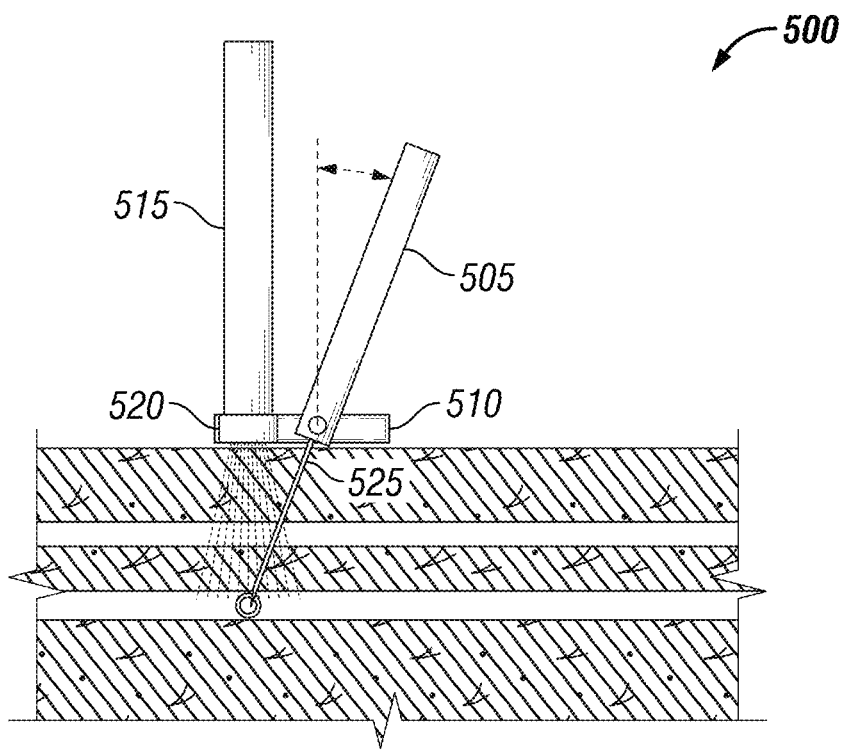

FIGS. 13A and 13B are illustrative implementations of a fourth arrangement for an insertion system 500. In insertion system 500, cartridge 505 has a variable angle in relation to boom 510. While cartridge 505 is shown independently attached to boom 510, in other implementations, cartridge 505 may be secured to fixed arm in a similar manner as to the articulating arm 45 shown in FIG. 4. Boom 510 is fixed near the bottom of transducer arm 515. Transducer arm 515 provides an attachment for transducer 520. Needle 525 is a variable length needle. As in the previous implementation, the angle of cartridge 505 and length of needle 525 are adjusted to achieve a desired target depth. A depth scale (not shown) for insertion system 500 takes into account the angle of cartridge 505. The depth scale may indicate the depth of needle 525 based on the angle of cartridge 505 and the amount needle 525 has been extended.

Figure 14A:
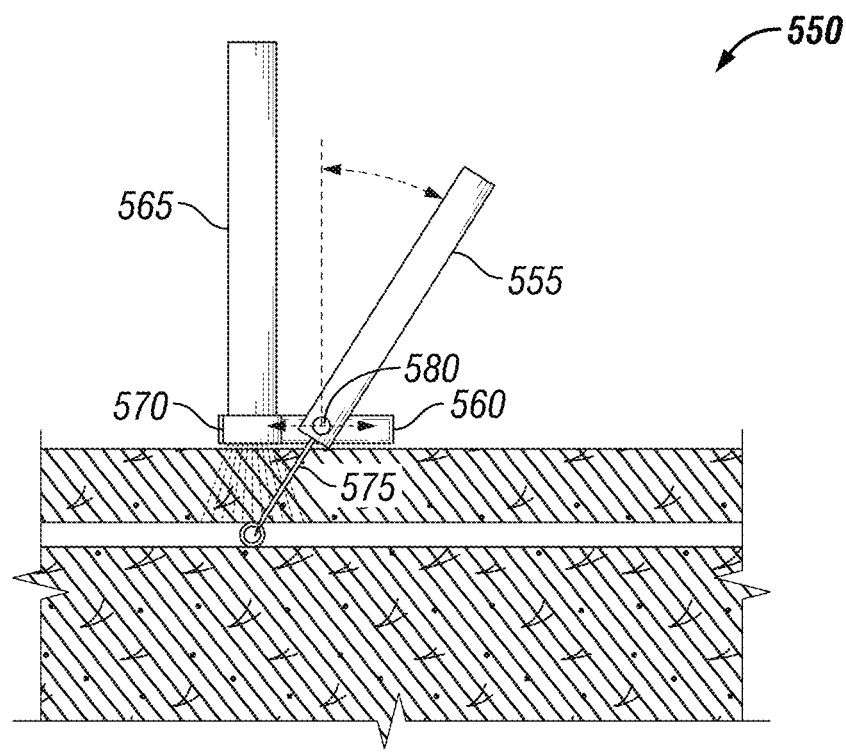
FIGS. 14A and 14B are illustrative implementations of a fifth arrangement for an insertion system.
Figure 14B:
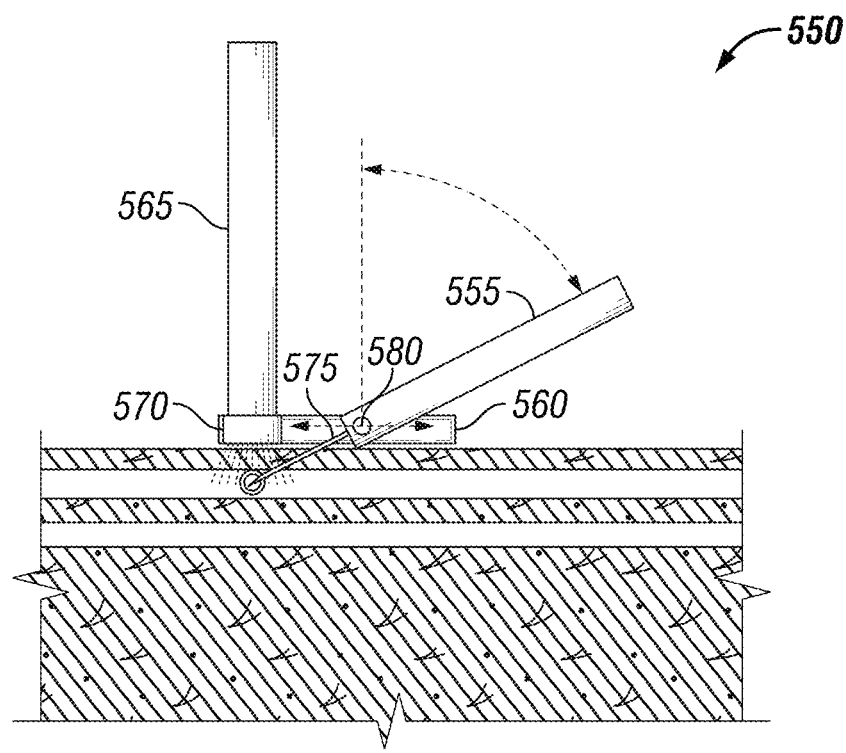

FIGS. 14A and 14B are illustrative implementations of a fifth arrangement for an insertion system 550. In insertion system 550, cartridge 555 has a variable angle in relation to boom 560. While cartridge 555 is shown independently attached to boom 560, in other implementations, cartridge 555 may be secured to fixed arm in a similar manner as to the articulating arm 45 shown in FIG. 4. Boom 560 is fixed near the bottom of transducer arm 565. Transducer arm 565 provides an attachment for transducer 570. Needle 575 is a fixed length needle. In contrast to the previous implementations, cartridge 555 has a variable pivot point 580 that can be moved along boom 560. The angle of cartridge 555 and variable pivot point 580 are adjusted to achieve a desired target depth. A depth scale (not shown) for insertion system 550 takes into account the angle of cartridge 555 and the variable pivot point 580.

Figure 15A:
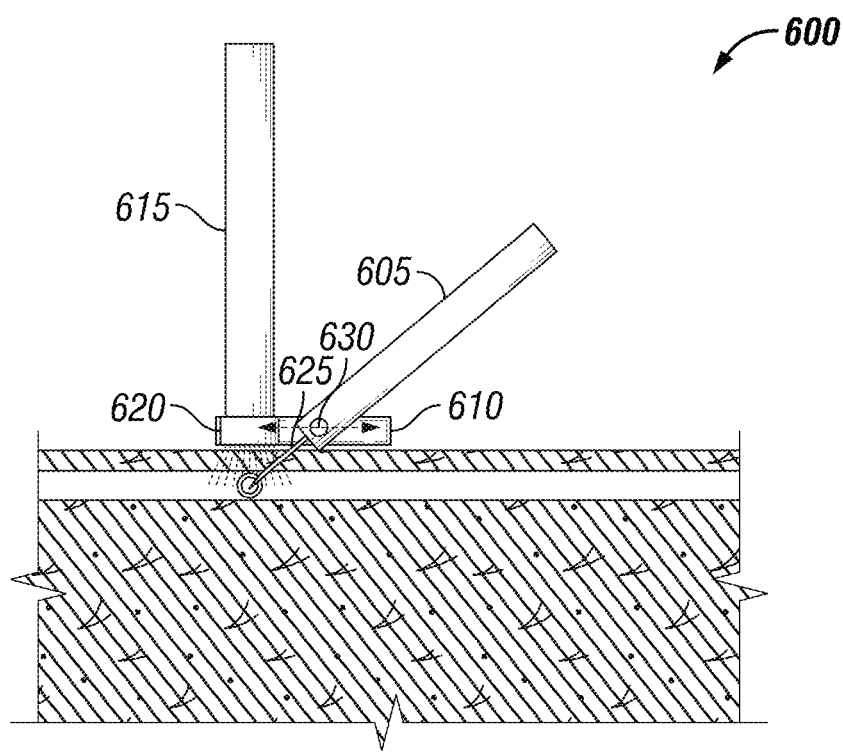
FIGS. 15A and 15B are illustrative implementations of a sixth arrangement for an insertion system.
Figure 15B:
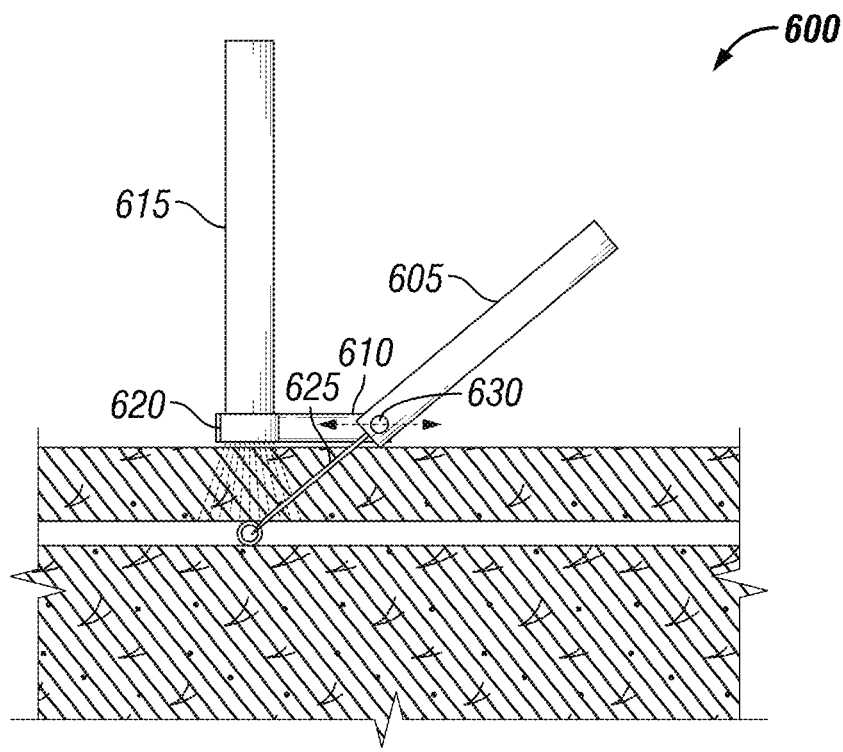

FIGS. 15A and 15B are illustrative implementations of a sixth arrangement for an insertion system 600. In insertion system 600, cartridge 605 has a fixed angle in relation to boom 610. While cartridge 605 is shown independently attached to boom 610, in other implementations, cartridge 605 may be secured to fixed arm in a similar manner as to the articulating arm 45 shown in FIG. 4. Boom 610 is fixed near the bottom of transducer arm 615. Transducer arm 615 provides an attachment for transducer 620. Needle 625 is a variable length needle. Cartridge 605 has a variable pivot point 630 that can be moved along boom 610. The variable pivot point 630 of cartridge 605 and length of needle 625 are adjusted to achieve a desired target depth. A depth scale (not shown) for insertion system 600 takes into account the a variable pivot point 630 and the amount needle 625 has been extended.

From the variety of arrangements discussed above, it should be noted that various arrangements may be also be suitable. For example, any suitable combination of a fixed/variable boom elevation, fixed/variable angle cartridge, fixed/variable needle length, and/or fixed/variable pivot point may be utilized.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. An apparatus for accessing the lumen of a vessel, the apparatus comprising:
    a main body providing an arc-like structure, wherein the main body comprises,
        an imaging device attachment adjacent to a pivot point positioned at a center of said arc-like structure, wherein the imaging device attachment is utilized to secure an image capturing instrument to the main body,
        a cartridge carrier coupled to said pivot point, wherein the cartridge carrier is adjustable to achieve a target insertion depth,
        a first motor coupled to the cartridge carrier, wherein the first motor adjusts the cartridge carrier to achieve the target insertion depth,
        a first actuator slideably coupled to said cartridge carrier, wherein the first actuator is coupled to a needle or sheath,
        a stop bar positioned on said main body in a sliding direction of the first actuator, and
        an extension extending from said first actuator, wherein said extension contacts said stop bar to impede advancement when said first actuator is advanced a predetermined length;
    a disposable cartridge attached to the cartridge carrier, wherein the disposable cartridge houses a guidewire, the needle, or the sheath for insertion into the vessel to the target insertion depth; and
    a first motor controller that operates the first motor, wherein the first motor controller is actuated to adjust the cartridge carrier to achieve the target insertion depth.

2. The apparatus of claim 1, wherein the disposable cartridge further comprises:
    a sliding truck slidably attached to the disposable cartridge, wherein the sliding truck is coupled to the needle in the disposable cartridge; and
    a sheath hub slidably attached to the disposable cartridge, wherein the sheath hub is coupled to the sheath in the disposable cartridge.

3. The apparatus of claim 2, wherein the main body further comprises a second actuator slideably coupled to said cartridge carrier, wherein the first actuator is coupled to the needle and the second actuator is coupled to the sheath.

4. The apparatus of claim 3, wherein the sliding truck is mated to the first actuator, and the sheath hub is mated to the second actuator.

5. The apparatus of claim 1, further comprises:
    a second motor coupled to a guidewire actuator provided by the cartridge carrier; and
    a guidewire disposed in the disposable cartridge, wherein the guidewire is advanced by the second motor and the guidewire actuator.

6. The apparatus of claim 1, further comprising:
    a needle motor coupled to the first actuator provided by the cartridge carrier; and
    the needle coupled to the first actuator, wherein the needle is advanced and retracted by the needle motor and the first actuator.

7. The apparatus of claim 1, further comprising:
    a sheath motor coupled to the first actuator provided by the cartridge carrier; and
    the sheath coupled to the first actuator, wherein the sheath is advanced and retracted by the sheath motor and the first actuator.

8. The apparatus of claim 1, further comprising an input controller for inputting the target insertion depth, wherein the main body automatically adjusts the cartridge carrier to a position corresponding to the target insertion depth.

9. The apparatus of claim 1, further comprising a screen overlay with a vertical line provided in the center of the screen overlay provided on a display of an imaging device.

10. The apparatus of claim 1, further comprising a depth scale arm that indicates insertion depths coupled to the main body and positioned opposite the pivot point, wherein the first motor controller is actuated to adjust the cartridge carrier along the depth scale to a position that corresponds to the target insertion depth.

11. A method for accessing the lumen of a vessel, the method comprising the steps of:
    attaching an image capturing instrument to an imaging device attachment of a main body providing an arc-like structure;
    attaching a disposable cartridge to the main body, wherein the main body comprises,
        an imaging device attachment adjacent to a pivot point positioned at a center of said arc-like structure, wherein the imaging device attachment is utilized to secure an image capturing instrument to the main body,
        a cartridge carrier coupled to said pivot point, wherein the cartridge carrier is adjustable to achieve a target insertion depth,
        a depth motor coupled to the cartridge carrier, wherein the depth motor adjusts the cartridge carrier to achieve the target insertion depth,
        a first actuator slideably coupled to said cartridge carrier, wherein the first actuator is coupled to a needle or sheath, a stop bar positioned on said main body in a sliding direction of the first actuator, and an extension extending from said first actuator, wherein said extension contacts said stop bar to impede advancement when said first actuator is advanced a predetermined length;

determining a depth of the vessel with an imaging device, wherein the depth of the vessel is the target insertion depth;

adjusting the cartridge carrier to achieve the target insertion depth; and actuating a controller, wherein the controller causes a guidewire, the sheath, or the needle in the disposable cartridge to advance a first predetermined distance.

12. The method of claim 11, wherein the image capturing instrument is an ultrasound transducer and the imaging device is an ultrasound imaging device.

13. The method of claim 11, wherein the main body further comprises a depth scale coupled the main body, wherein the depth scale is an arm positioned opposite the pivot point indicating insertion depths, and the depth motor is actuated to adjust a position of the cartridge carrier on the depth scale.

14. The method of claim 11, wherein the controller is a sheath controller coupled to a sheath motor that advances and retracts the sheath.

15. The method of claim 11, wherein the controller is a needle controller coupled to a needle motor that advances and retracts the needle.

16. The method of claim 15, further comprising the step of:

actuating a guidewire controller to advance the guidewire; and actuating the needle controller to retract the needle.

17. The method of claim 16, further comprising the step of:

actuating a sheath controller to advance the sheath to the target insertion depth; and removing the sheath from the disposable cartridge.

18. The method of claim 16, wherein the needle and a sliding truck are advanced and retracted by a needle motor.

19. The method of claim 16, wherein the guidewire is advanced by a guidewire motor.

20. The method of claim 11, further comprising the step of placing a screen overlay on a display of the imaging device.

* * * * *